United States Patent
Parker et al.

(10) Patent No.: US 7,001,980 B1
(45) Date of Patent: Feb. 21, 2006

(54) MONOCLONAL ANTIBODIES DIRECTED AGAINST THE G3BP PROTEIN, AND USES

(75) Inventors: Fabienne Parker, Antony (FR); Mireille Kenigsberg, Montgeron (FR); Marc Duchesne, Sucy en Brie (FR); Isabelle Barlat, La queue en Brie (FR)

(73) Assignee: Aventis Pharma S.A., Antony (FR)

( * ) Notice: Subject to any disclaimer, the term of this patent is extended or adjusted under 35 U.S.C. 154(b) by 0 days.

(21) Appl. No.: 09/719,758

(22) PCT Filed: Jun. 17, 1999

(86) PCT No.: PCT/FR99/01453

§ 371 (c)(1),
(2), (4) Date: Jan. 4, 2002

(87) PCT Pub. No.: WO99/65947

PCT Pub. Date: Dec. 23, 1999

(30) Foreign Application Priority Data

Jun. 17, 1998 (FR) .................................. 98 07617

(51) Int. Cl.
*C07K 16/00* (2006.01)
*C07K 16/18* (2006.01)

(52) U.S. Cl. ............................... 530/187.1; 530/388.1; 435/326

(58) Field of Classification Search ............. 530/387.1, 530/387.3, 388.1, 388.8, 388.85, 187.1; 424/130.1, 424/141.1, 155.1, 156.1; 435/326
See application file for complete search history.

(56) References Cited

U.S. PATENT DOCUMENTS

| | | | |
|---|---|---|---|
| 5,783,186 A | * | 7/1998 | Arakawa et al. |
| 5,886,150 A | * | 3/1999 | Duchesne et al. |
| 6,252,050 B1 | * | 6/2001 | Ashkenazi et al. |
| 6,458,356 B1 | * | 10/2002 | Arakawa et al. |

FOREIGN PATENT DOCUMENTS

WO   95/01539   5/1996

OTHER PUBLICATIONS

Schaffhausen, Hybridoma Technology in the biosciences and medicine, Plenum press, chapter 21, pp. 355-373, 1985.*
Paul, Fundamental Immunology, Raven Press, NY, chapter 8, p. 242, 1993.*
Harlow et al, Antibodies, a Laboratory Manual, Cold spring Harbor Laboratory, chapter 6 and 7, 1988.*
Duchesne et al., Identification of the SH3 Domain of GAP as an Essential Sequence for Ras-GAP-Mediated Signaling, Science, 259, 525-528 (1993).
Parker, Fabienne et al., A Ras-GTPase-Activating Protein SH3-Domain-Binding Protein, Molecular and Cellular Biology, Jun. 1996, 16, 2561-2569.

* cited by examiner

*Primary Examiner*—Sheela J. Huff
*Assistant Examiner*—Lei Yao
(74) *Attorney, Agent, or Firm*—Karen I. Krupen

(57) ABSTRACT

The invention concerns monoclonal antibodies directed against the G3BP protein and cell lines producing them. The invention also concerns the use of said antibodies or their derivatives for obtaining medicines and diagnostic reagents.

5 Claims, 5 Drawing Sheets

Figure 1:
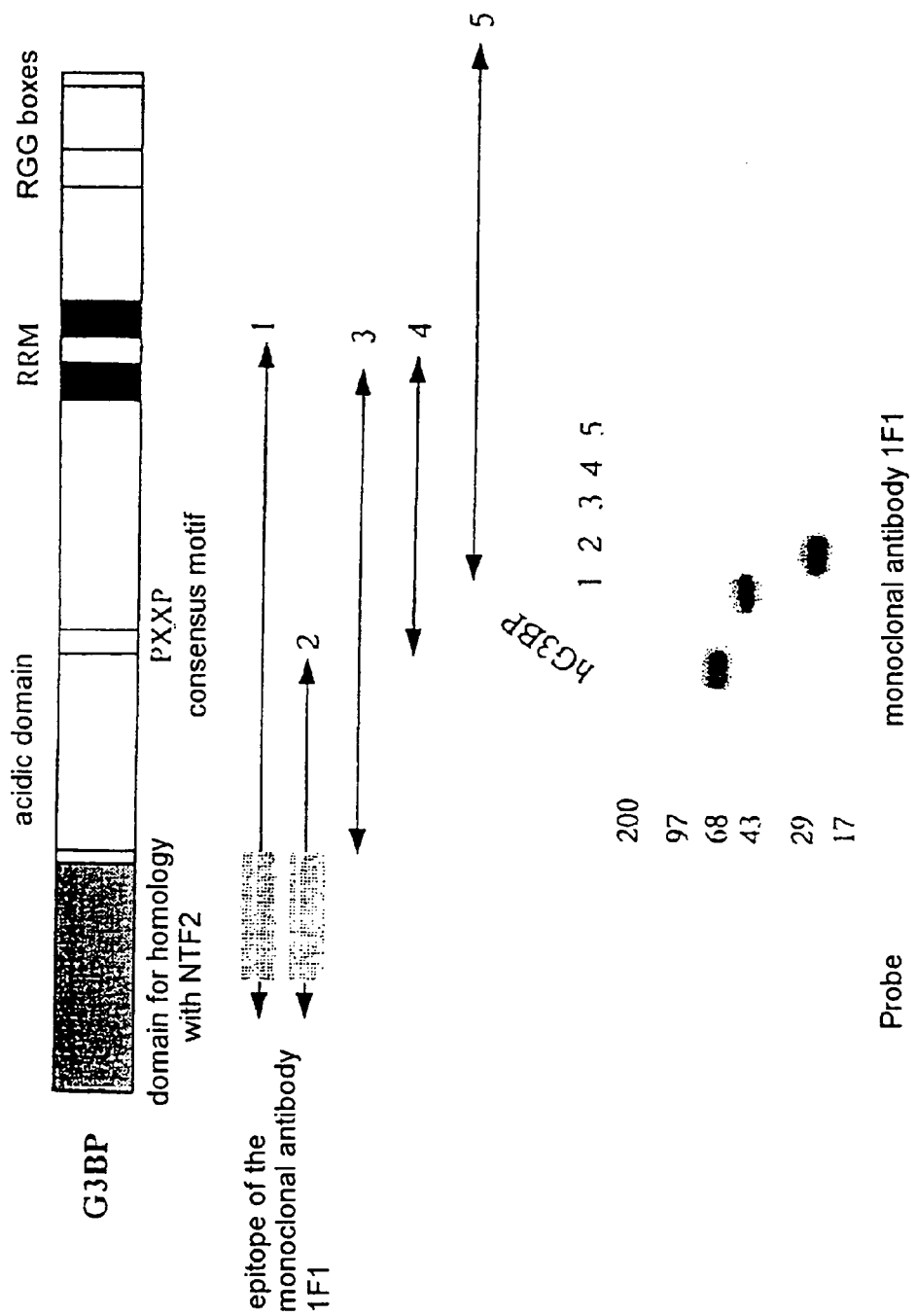

P1: Polyp
P2: Moderately Differentiated Adenocarcinoma
P3: Well-differentiated adenocarcinoma

```
G3BP    MVMEKPSPLLVGREFVRQYYTLLNQAPDMLHRFYGKNSSYVHGGLDSNGKPADAV
                 : ::                :          : ::       : ::
G3BP2   MVMEKPSPLLVGREFVRQYYTLLNKAPEYLHRFYGRNSSYVHGGVDASGKPQEAV
                 10        20        30        40        50

G3BP    YGQ KEIHRKVMSQNFTNCHTKIRHVDAHATLNDGVVVQVMGLLSNNNQALRRFMQ
         : ::                                : ::
G3BP2   YGQNDIH HKVL SLNFSECHTKIRHVDAHATLSDGVVV QVMGLLSNSGQPERKFMQ
               60        70        80        90       100       110

G3BP    TFVLAPEGSVANKFYVHND I FRYQDEVFGGFVT
                            : ::       : ::
G3BP2   TFVLAPEGSVPNKFYVHNDMFRYEDEVFGDSEP
               120       130       140
```

FIGURE 4

MONOCLONAL ANTIBODIES DIRECTED AGAINST THE G3BP PROTEIN, AND USES

The present invention relates to monoclonal antibodies directed against the G3BP protein and the cell lines producing them. The invention also relates to the use of these antibodies or their derivatives for obtaining medicines and diagnostic reagents.

The products of the ras genes, generally designated p21Ras proteins, play a key role in controlling cell division in all eukaryotic organisms where they have been tested for. Certain specific modifications of these proteins cause them to lose their normal control and lead them to become oncogenic. Thus, a large number of human tumours have been associated with the presence of modified ras genes. Likewise, an overexpression of the p21Ras proteins can lead to a disruption of cell proliferation. Overall, the p21Ras proteins are involved in 30% of human cancers.

An understanding of the exact role of these p21Ras proteins therefore constitutes one of the target objectives of research in the field of oncology.

The model currently available for explaining the function of the p21Ras proteins is based on analogies which they share with transduction G proteins. An equilibrium exists in the cells between the active p21 proteins, bound to GTP, and the inactive forms, which have bound GDP. In a quiescent cell, where the Ras proteins are not called into play, most of them are in the GDP form. When the cell is stimulated, the nucleotide exchange factor, GEF, becomes more active and facilitates the evacuation of GDP and its replacement with GTP. The protein then adopts an active conformation which allows it to recognize and stimulate its effector, the GAP protein "GTPase activating protein". The Ras-GTP-GAP complex probably interacts, in turn, with a protein or with other proteins, thus allowing the transmission of the signal which causes a biological response of the cell. The combination of Ras-GTP with GAP simultaneously triggers the hydrolysis of GTP and the return of the Ras protein to its inactive, GDP form.

In the case of the oncogenic p21Ras proteins, the mutation which they carry prevents the return to the inactive state. The equilibrium is in the latter case shifted towards the active form of Ras.

This complex equilibrium between the active and inactive forms of p21Ras is controlled both by factors inherent to the biochemical properties of the Ras proteins (relative affinity for GDP and GTP, rate of exchange of nucleotides and the like) and external factors which modulate their activity, such as in particular the GAP protein.

The GAP protein is a cytosolic protein present in all eukaryotic organisms which therefore possesses the ability to greatly accelerate the hydrolysis of GTP, which is bound to the normal p21 protein (Trahey and McCormick 1987). It possesses two domains which provide distinct functions. Its carboxy-terminal end carries the catalytic activity which binds the Ras proteins and increases their GTPase activity. At its other end, downstream of the amino-terminal part, is a juxtaposition of SH2 and SH3 domains which are capable of participating in interactions with other proteins.

The applicant has already identified an additional protein in the Ras-dependent signalling cascade. Thus, application WO 96/16169 describes the identification, cloning, sequencing and characterization of a protein capable of binding the SH3 domain of GAP, designated G3BP ("GAP-SH3 Binding Protein"). This application shows in particular that G3BP is an effector for GAP, that is to say a partner which plays a role downstream in the Ras-dependent signalling pathway. Thus, the article by Parker et al. (Mol. Cell. Biol. 16 (1996) 2561) describes the sequence of this protein, its GAP-binding capacity and the like. This protein constitutes a major new target in the development of anticancer therapeutic approaches.

The G3BP protein is a ubiquitously expressed cytosolic protein of 68 kDa. The sequence of the G3BP protein and of the corresponding gene are presented in SEQ ID No. 1 and SEQ ID No. 2. This protein of 466 amino acids belongs to the hnRNP (heterogeneous nuclear RiboNucleoproteins) family and contains several domains characteristic of proteins which bind to RNA:
- an RRM domain (aa 342–385) with the RNP2 (aa 342–347) and RNP1 (aa 378 to 385) domains
- a domain rich in the amino acids Arginine and Glycine (aa 429 to 461)
- an acidic auxiliary domain (aa 144 to 221)

The applicant has now become interested in the mechanism of action of the G3BP protein. Accordingly, the applicant obtained various antibodies directed against various domains of the G3BP protein in order to antagonize the G3BP activity or to constitute G3BP effectors.

The present invention is based, on the one hand, on the demonstration of an overexpression of the G3BP protein in tumour cells and in human tumours (colon adenocarcinoma and breast tumour) and, on the other hand, on the surprising discovery that some antibodies directed against the G3BP protein are capable of inducing apoptosis in human tumour cells. Unexpectedly, it has been observed that these antibodies induce apoptosis in tumour cells in which the G3BP protein is overexpressed but are found to be nontoxic in normal human cells where G3BP is weakly expressed.

A first subject of the invention relates to monoclonal antibodies directed against the G3BP protein and capable of inducing apoptosis in various types of tumour cells.

More particularly, the subject of the invention is monoclonal antibodies capable of recognizing an epitope situated in the N-terminal portion of the G3BP protein. Advantageously, this includes an epitope between the amino acids situated at positions 1 and 144 of the G3BP protein and preferably this includes an epitope between the amino acids situated at positions 1 to 72 of the G3BP protein. Preferably still, this includes an epitope between the amino acids situated at positions 22 to 55 of the G3BP protein, and more preferably still an epitope consisting of the amino acids situated at positions 22–34.

In a particularly advantageous embodiment, the present invention relates to antibodies designated by the name Mab 1F1 and secreted by the hybridoma line G3B 1F1 1D1 deposited on 9 Jun. 1998 at the C.N.C.M. under the number I-2038.

The invention also includes the antibodies derived from the monoclonal antibodies defined above. For the purposes of the present invention, the expression derived antibodies is understood to mean any molecule which comprises the idiotype for the monoclonal antibodies according to the invention and in particular the chimeric antibodies, the single-chain antibodies and the Fab fragments. Such chimeric antibodies may be obtained according to the techniques described by Morrison et al., J. Bacteriol. 159: 870 (1984); Neberger et al., Nature 312:604–608 (1984); Takeda et al., Nature 314:452–454 (1985), which are incorporated herein by way of reference. The Fab fragments which contain the idiotype for the antibodies according to the invention may be generated by any technique known to persons skilled in the art. For example, such fragments comprise, without limitation: the F(ab')$_2$ fragment, a fragment which may be produced by digestion with pepsin from the antibody; the Fab' fragments which may be obtained by reduction of the disulphide bridges of the F(ab)$_2$ fragment, and the Fab fragments which may be produced by treating the antibody with papain and a reducing agent.

The subject of the invention is also single-chain antibodies ScFv derived from the monoclonal antibodies defined above. Such single-chain antibodies may be obtained according to the techniques described in U.S. Pat. Nos. 4,946,778, 5,132,405 and 5,476,786.

The invention also relates to a nucleic acid sequence comprising a gene encoding a single-chain antibody derived from the monoclonal antibodies described above. The production of such sequences and their use for the in vivo expression of antibodies has been described in application WO 94/29446 incorporated herein by way of reference.

The subject of the invention is also viral or plasmid vectors containing a nucleic acid sequence encoding a single-chain antibody derived from the monoclonal antibodies described above. More particularly, the vectors of the invention are of viral origin, such as retroviruses, adenoviruses, adeno-associated viruses, herpes virus, vaccinia virus, HSV virus and the like.

The invention also relates to the use of nucleic acid sequences encoding these ScFv or of vectors containing them for the preparation of pharmaceutical compositions intended for the surgical or therapeutic treatment of the human or animal body. It also relates to any pharmaceutical composition comprising a vector, especially a viral vector, or a nucleic acid sequence as defined above.

The subject of the invention is also the hybridoma lines capable of secreting the monoclonal antibodies according to the invention.

The subject of the invention is more particularly the hybridoma line G3B 1F1 1D1 secreting the antibody Mab 1F1 deposited on 9 Jun. 1998 at the Collection Nationale des Cultures de Microorganismes (C.N.C.M.) under the number I-2038.

The invention also relates to a method of producing monoclonal antibodies capable of inducing apoptosis in various tumour lines comprising (1) the fusion of spleen cells from an animal immunized with the aid of the G3BP protein or of a fragment comprising at least a portion of the N-terminal domain (aa 1–144), with myelomatous cells under conditions allowing the formation of hybridomas; (2) the detection and isolation of those of the said hybridomas which secrete monoclonal antibodies capable of inducing apoptosis in various tumour lines.

The invention also relates to the use of the antibodies defined above for obtaining medicines. The invention relates more particularly to the use of the said antibodies for obtaining a medicine intended for the treatment or prevention of hyperproliferative disorders.

The subject of the invention is also pharmaceutical compositions comprising a therapeutically effective quantity of the antibodies according to the invention, optionally mixed with a pharmaceutically acceptable carrier, the said quantity being therapeutically effective for inducing apoptosis in tumour cells.

The antibodies according to the invention may also be used as diagnostic reagent for identifying or assaying the G3BP protein. Indeed, it has been observed that the G3BP protein is overexpressed in tumour cells and that this overexpression constitutes a marker in cell proliferation phenomena. These antibodies are therefore particularly useful for the diagnosis of hyperproliferative diseases causing overexpression of the G3BP protein.

The subject of the invention is therefore also the use of the monoclonal antibodies defined above as diagnostic reagent and a kit for immunological diagnosis comprising the said monoclonal antibodies.

The antibodies may be coupled to chromogenic, fluorescent, biotinylated or radioactive markers and the like. The antibodies may be used in immunolabelling methods in immunohistochemistry, in flow cytometry, for radioimmunological assays (RIA) or immunoenzymatic assays (ELISA) and in any known type of diagnostic kits.

The antibodies according to the invention have also made it possible to carry out a functional study of the G3BP protein. In particular, this functional study has led to the identification of new peptides derived from the G3BP protein and which exhibit an apoptotic activity. In this regard, the subject of the invention is also new peptides derived from the G3BP protein and capable of inducing apoptosis. Preferably, the peptides according to the invention comprise the N-terminal fragment, and preferably still these polypeptides comprise at least the domain corresponding to the first 14 amino acids of the G3BP protein.

In addition to the preceding arrangements, the present invention also comprises other characteristics and advantages which will emerge from the examples which follow, and which should be considered as illustrating the invention without limiting the scope thereof.

LEGEND TO THE FIGURES

FIG. 1: Western Blot identification of various domains of G3BP which are recognized by the antibody Mab 1F1

Figure 2A:
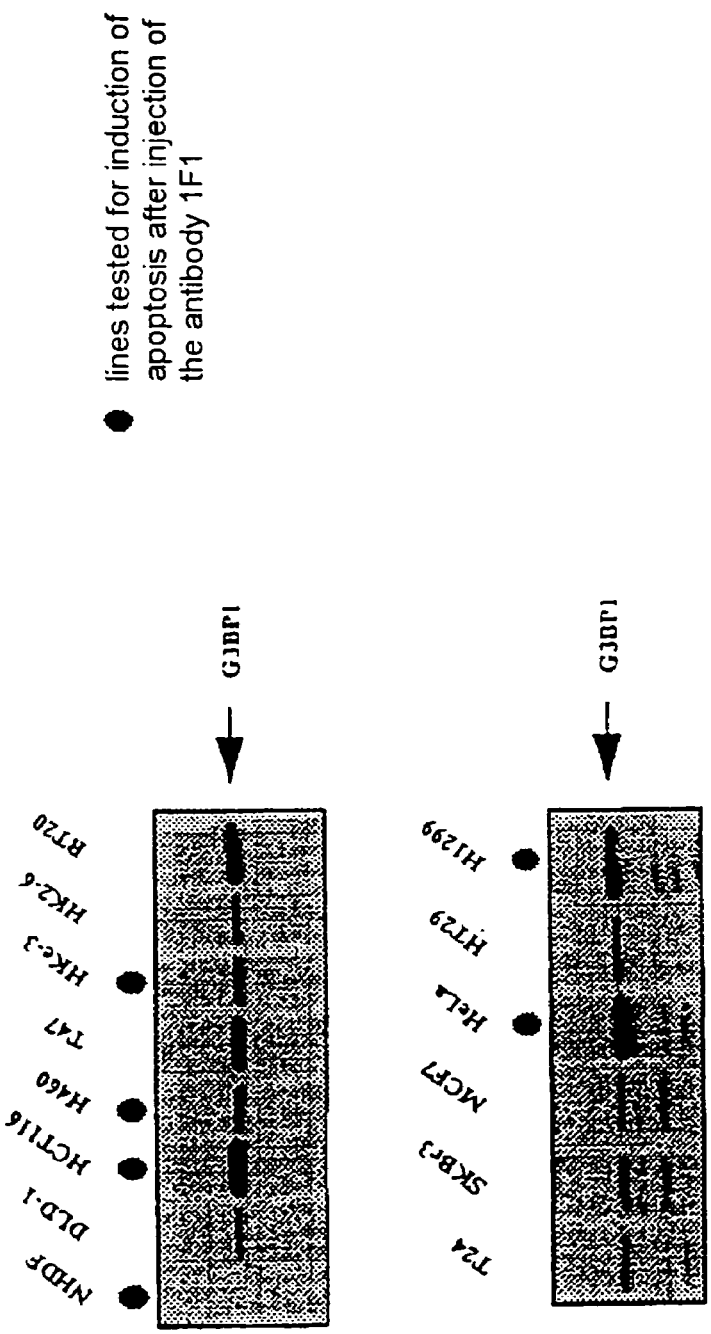
Figure 2B:
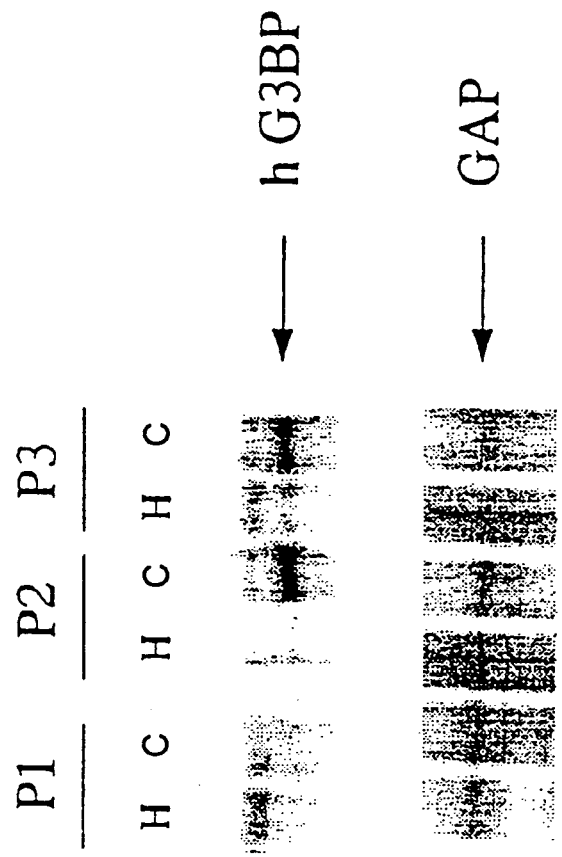

FIG. 2a and FIG. 2b: Comparison of the level of expression of the G3BP protein in various cell lines.

Figure 3:
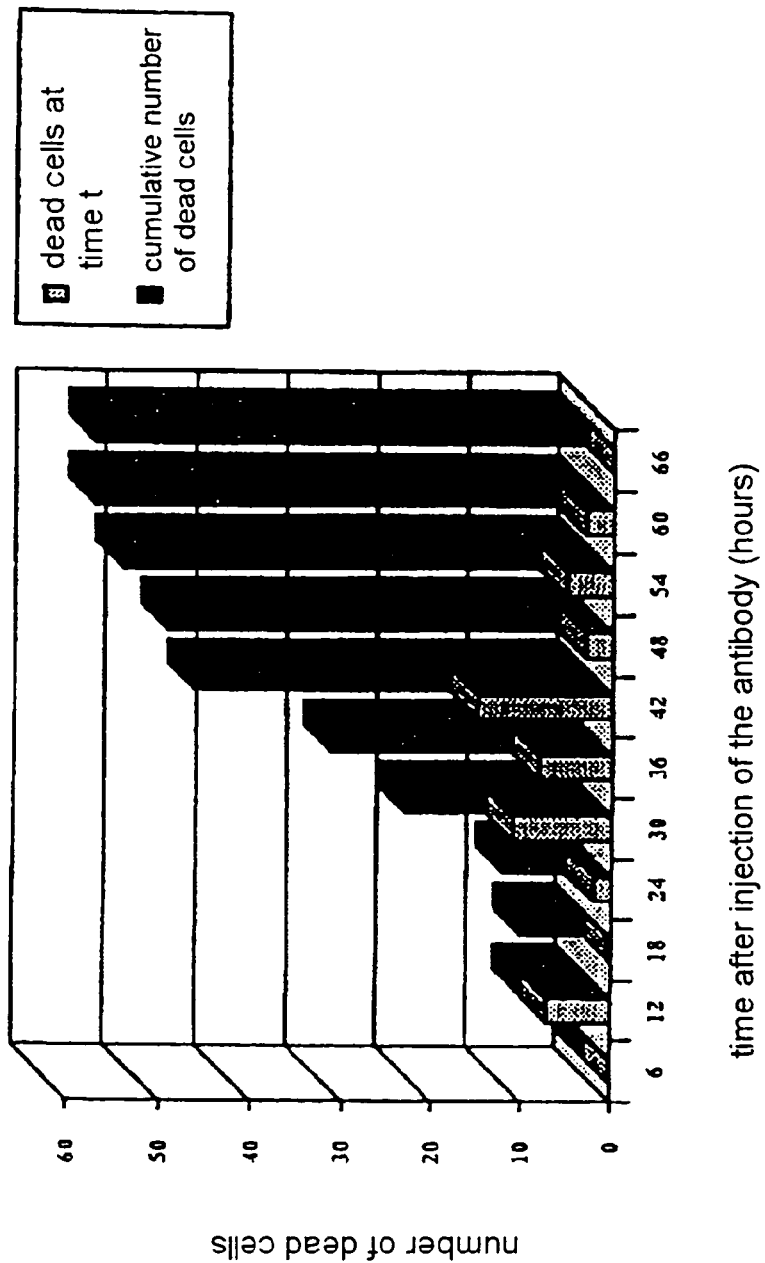

FIG. 3: Effect of the microinjection of the antibody Mab 1F1 into HCT116 cells.

FIG. 4: Comparison of sequences between the human G3BP (SEQ ID NO:3) and G3BP2 (SEQ ID NO:4) proteins. The comparison of the N-terminal sequences reveals several differences which are identified by diaereses.

MATERIALS AND METHODS

Cell Lines Used

HCT116: epithelial cells derived from human colon carcinoma exhibiting a mutated Ki-ras gene and a mutation in the tumour suppressor gene DCC. Culture medium required: DMEM, 10% foetal calf serum, 1% Penicillin/Streptomycin, 1% Glutamine.

Hke-3 and HK2-6: HCT116 cells modified by deletion of the Ki-ras gene and which have, as a result, lost their tumorigenic power (ref: Shirasawa, . . . Sasazuki (1993) Science 260, 85–88). Culture medium required: DMEM, 10% foetal calf serum, 400 μg/ml Geneticin, 1% Penicillin/Streptomycin, 1% Glutamine.

H460: epithelial cells derived from human non-small cell lung carcinoma having a mutated Ki-ras gene. Culture medium required: DMEM, 10% foetal calf serum, 1% Penicillin/Streptomycin, 1% Glutamine.

H1299: origin ATCC. Epithelial cells derived from human lung carcinoma exhibiting a mutated N-ras gene and a deletion of the p53 gene. Culture medium required: DMEM, 10% foetal calf serum, 1% Penicillin/Streptomycin, 1%. Glutamine.

HeLa: epithelial cells derived from human cervical carcinoma exhibiting no mutation of the ras genes. Culture medium required: DMEM, 10% foetal calf serum, 1% Penicillin/Streptomycin, 1% Glutamine.

HT-29: origin ATCC. Epithelial cells derived from human colon carcinoma exhibiting a mutation of the p53 gene but no mutations of the ras genes. Culture medium required: DMEM, 10% foetal calf serum, 1% Penicillin/Streptomycin, 1% Glutamine.

DLD-1: origin ATCC. Epithelial cells derived from human colon carcinoma exhibiting a mutation of the Ki-ras gene and of the p53 gene. Culture medium required: DMEM, 10% foetal calf serum, 1% Penicillin/Streptomycin, 1% Glutamine.

T47: origin ATCC. Cells isolated from pleural effusion from a patient suffering from a mammary carcinoma. Culture medium required: RPMI, 10% foetal calf serum, 1% Penicillin/Streptomycin, 1% Glutamine.

BT20: cells derived from human mammary carcinoma. Culture medium required: RPMI, 10% foetal calf serum, 1% Penicillin/Streptomycin, 1% Glutamine.

MCF-7: cells derived from human mammary carcinoma. Culture medium required: RPMI, 10% foetal calf serum, 1% Penicillin/Streptomycin, 1% Glutamine.

T24: origin ATCC. Cells derived from human bladder carcinoma, exhibiting a mutation of the Ha-ras gene. Culture medium required: RPMI, 10% foetal calf serum, 1% Penicillin/Streptomycin, 1% Glutamine.

NHDF: origin Boerhinger Ingelheim, Normal Human Dermal Fibroblasts (adult) in primary culture having no mutated genes. Supplier's required medium.

EXAMPLES

Example 1

Production of Monoclonal Antibodies 1.1—Production of the G3BP Protein

The cultures of SF9 cells were carried out according to the protocol described in Parker et al. (Mol. Cell. Biol. 16 (1996) 2561). The cells are lysed in the presence of HNTG buffer (50 mM Hepes, pH 7.5, 150 mM NaCl, 1% Triton ×100, 10% Glycerol, 1 mM % g Cl2, 1 mM EGTA; in the presence of phosphatase inhibitors (1 mM Na3VO4, 10 mM Na4P2O7, 10 mM NaF) and of protease inhibitors (1 $\mu$g/ml of leupeptin, 1 $\mu$g/ml of trypsin inhibitor, 1 $\mu$g/ml of pepstatin A, 2 $\mu$g/ml of aprotinin, 10 $\mu$g/ml of benzamidine, 1 mM phenylmethanesulphonyl fluoride, 1 $\mu$g/ml of antipain, 1 $\mu$g/ml of chymostatin). The lysate is centrifuged (15 000 g, 15 min) and diluted 5-fold in HG washing buffer (50 mM Hepes pH 7.5, 10% glycerol, 1 mM EGTA, in the presence of phosphatase inhibitors and of protease inhibitors). The lysate is then incubated for 12 hours in the presence of Heparin-Sepharose Fast Flow gel (Pharmacia LKB) in an amount of 15 mg of protein per milliliter of gel, equilibrated in the same buffer (50 mM Hepes, 0.030 M NaCl, 0.2% Triton ×100, 10% glycerol, 1 mM MgCl2, 1 mM EGTA). The complex is transferred onto a Pharmacia K26 column. The column is washed with 10 volumes of equilibration buffer (50 ml/hour), and then the proteins are eluted in 100 mM NaCl buffer and then in 600 mM NaCl buffer. The fractions containing the GAP-SH3 binding activity are combined, diluted 10-fold in HG buffer and loaded onto an agarose-polyribouridylic acid AGPOLY(U) column, (type 6 column, 19 cm$^2$×1 cm, Pharmacia) in an amount of 1.3 mg of protein per milliliter of gel. The column is pre-equilibrated in the same buffer with a flow rate of 5 ml/cm$^2$ h$^{-1}$. After washing in HNG buffer (60 mM NaCl), the contaminating proteins are eluted with 229 ml of a buffer in a linear gradient from 0.06 to 0.32 M NaCl, and the G3BP protein is eluted in the presence of 0.7 M NaCl. After the POLY(U) chromatography, the fractions containing the G3BP protein are combined, diluted 12-fold in the presence of phosphate buffer pH 7.5+protease inhibitors) and loaded onto a 1 ml MonoS HR5/5 column (Pharmacia), pre-equilibrated in the same buffer containing 60 mM NaCl, at a flow rate of 30 ml h$^{-1}$. After rinsing the column, the proteins are eluted with 40 ml of a buffer in a linear gradient from 0.06 to 1 M NaCl. The G3BP protein is eluted between 0.15 M and 0.2 M NaCl.

1.2—Protocol for Immunizing the Mice 6-week-old female BALB/c mice received an intraperitoneal injection of 25 $\mu$g of G3BP on day D0 of immunization. A second intraperitoneal injection was made on day D14 of immunization and then a third and a fourth injection on days D45 and D80. A fifth injection (10 $\mu$g of G3BP protein) was made by the intravenous route on day D165 and the splenocytes were extracted three days later and fused. The splenocytes were fused with murine myeloma cells SP2/O-Ag14 on the one hand and X63Ag8/653 on the other hand. The splenocyte/myeloma cell ratio is 5:1. Lymphocytic hybridization is carried out in the presence of polyethylene glycol PEG pm 1 500 (final concentration 40%). 16 plates of 96 wells were prepared in the presence of 10 000 Balb/C mouse peritoneal macrophages per well. The quantities of splenocytes used vary between 2.5×10$^4$ and 10$^5$ cells per well. The medium used contains RPMI 1640 (Biowhittaker and Gibco), 2 mM glutamine, 1 mM sodium pyruvate, HAT, 100 mM hypoxantine, 0.4 $\mu$M aminopterin, 16 $\mu$M thymidine, 220% decomplementized foetal calf serum, 100 U/ml penicillin, 100 $\mu$g/ml streptomycin.

The first clones appear three days after the fusion, the medium is changed seven days after the fusion, and finally, 10 days after the fusion, 5 000 macrophages are added per well. The wells in which a single hybridoma has grown are identified and the supernatants are collected for screening.

The hybridoma supernatants obtained from the fusion are screened by Western Blotting. Cell extracts (50 $\mu$g) of ER22 cells and of HCT116 cells, the recombinant G3BP protein and a control protein SAM68 were subjected to sodium dodecyl sulphate —7.5% polyacrylamide gel electrophoresis (SDS-PAGE) and then transferred onto a polyvinylidene difluoride membrane (PVDF Millipore Corpo.). Nonspecific binding is blocked with 2% skimmed milk in ECL buffer (20 mM Tris, pH 7.4, 150 mM NaCl, 0.05% Tween 20) for 2 hours, at room temperature.

The membranes are then incubated with the various supernatants diluted 1/50 in the blocking buffer overnight at 4° C. After washing with ECL buffer—0.05% Tween 20, the bound proteins are detected by incubation with an anti-mouse antibody conjugated to a peroxidase and ECL chemiluminescent reagent (NEN Life Science Product).

Three hybridomas were selected at the end of this screening. They are the hybridomas G3B 1E1, G3B 1F1 1D1 and G3B1 1H7.

Example 2

Identification of the Epitope Recognized by the Antibody Mab 1F1

Various fragments of the G3BP protein were produced in a system for expression in insect cells (SF9) infected with a recombinant baculovirus according to the technique described in Parker et al. (Mol. Cell. Biol. 16 (1996) 2561). They are the fragments "1" (aa 72–350), "2" (aa 72–235), "3" (aa 144–341), "4" (aa 236–350) and "5" (aa 299–466).

Western blot experiments were carried out using these fragments produced in a baculovirus system.

2.1—Detection of the Proteins by Western Blotting

After removing the culture medium, the proliferating cells are washed twice in phosphate buffer at 4° C. The lysis is carried out directly on the culture dishes in the presence of 1 ml of HNTG buffer (50 mM HEPES pH 7.5, 150 mM NaCl, 1% Triton x-100, 10% glycerol, 1 mM MgCl2, 1 mM+phosphatase inhibitors (1 mM $Na_3VO_4$, 10 mM $Na_4P_2O_7$, 10 mM NaF)+protease inhibitors (1 μg/ml leupeptin, 1 μg/ml trypsin inhibitor, 1 μg/ml pepstatin A, 10 μg/ml benzamidine, 1 mM phenylmethylsulphonyl fluoride, 1 μg/ml antipain, 1 μg/ml chymostatin). The proteins are separated on a Sodium Dodecyl Sulphate (SDS)-7.5% polyacrylamide (PAGE) acrylamide electrophoresis gel (16 hours, 60 volts), the proteins are then transferred onto polyvinylidene difluoride membrane (PVDF) Millipore Corp.) by a semiliquid transfer method. The transfer is carried out at 4° C., for 3 hours, at a voltage of 60 volts, in a transfer buffer containing 25 mM Tris Base, Glycine 192, 0.15% SDS 20% methanol. The membrane is rinsed in PBS and then saturated in PBS supplemented with 0.05% tween 20 and with 2% skimmed milk for 2 hours at room temperature. The membrane is incubated for 12 h at 4° C., in an ECL buffer (20 mM TRIS, pH 7.4, 150 mM NaCl)+0.05% Tween 20+2% skimmed milk, containing the first antibody. The antibody MAB 1F1 is diluted 1/10 000. The membrane is then rinsed 4 or 5 times for 10 minutes, at room temperature in an ECL buffer+0.05% Tween 20. The second antibody (anti-mouse antibody) is then added in the presence of ECL+0.05% Tween 20 for 45 minutes at room temperature. The antibodies are coupled to peroxidase which allows visualization of the proteins by the Enhanced ChemiLuminescence (ECL) technique. The membrane is rinsed 4 or 5 times in PBS buffer+0.05% Tween 20, incubated for 1 minute in the ECL reagent. The visualization is carried out according to the supplier's recommendations (NEN Life Science Product).

The results are presented in FIG. 1 and show that the antibody Mab 1F1 allows the detection of fragments "1" (aa 72–350) and "2" (aa 72–235). The central fragment "3" (aa 144–341) comprising a common zone with fragment "2" is not recognized. Fragments "4" (aa 236–350) and "5" (aa 299–466) are not recognized either.

These results show that the epitope recognized by the antibody Mab 1F1 is located in the N-terminal region of the G3BP protein, in the zone corresponding to the first 144 amino acids and more particularly in the zone comprising the first 100 amino acids situated upstream of the acidic domain (aa 144–221) of the G3BP protein.

Example 3

Level of Expression of the G3BP Protein in Various Cell Lines

The level of expression of the G3BP protein was studied in human colorectal tumours and in various tumour lines.

3.1—Level of Expression of G3BP in Various Human Cell Lines

For this experiment, the cells in culture are harvested by scrapping and centrifuged for 5 min at 2 000 rpm so as to collect them in pellet form. They are then lysed in a 10 mM Hepes buffer pH 7.2, 140 mM KCl, 5 mM $MgCl_2$, 0.2% NP40 and protease inhibitors for 45 min at 4° C. The lysates are centrifuged at 14 000 rpm for 10 min and the supernatants are collected. An assay of proteins is carried out and the supernatants are denatured in 4× Laemmli buffer and treated for 10 min at 95° C.

The equivalent of 50 μg of proteins of different lysates is deposited per well of a 10% acrylamide SDS-PAGE Novex minigel, 10 wells and 1.5 mm in thickness.

After migration, electrotransfer onto PVDF membrane and passivation of the membranes in TTBS buffer [20 mM TRIS pH 7.5, 150 mM NaCl, 0.1% Tween 20, 0.02% sodium azide] containing 3% BSA, the samples are subjected to Western blotting:

The membranes are incubated for 2 hours with the antibody Mab 1F1 diluted to 0.2 μg/ml in TTBS buffer containing 3% BSA, they are then rinsed four times with TTBS for 10 min, and then incubated for 1 hour with a peroxidase-labelled anti-mouse antibody and again rinsed four times with TTBS for 10 min. The membranes are then visualised with the NEN-Dupont ECL kit (chemiluminescence) on an Amersham ECL film.

The results are presented in FIG. 2a. The film obtained shows the overexpression of the G3BP protein in all the tumour lines tested, relative to the normal fibroblast line NHDF. The level of this overexpression is variable from one line to another but is not dependent on the state of activation of the ras genes in these lines; the cell lines having a mutated Ki-ras gene such as HCT116, H460 or DLD-1 express more or less strongly the G3BP protein and the cell lines exhibiting no mutation of the ras genes such as HeLa or HT29 have an equally high and variable G3BP expression level.

It is possible however to observe that the level of expression of G3BP is reduced in the HKe-3 and HK2-6 cells in which the Ki-ras gene has been deleted, relative to the cells from which they are derived, HCT116, without this expression being abolished as a result.

Level of Expression of G3BP in Human Biopsies

Samples of healthy or tumour tissues were fixed on a slide. Solubilization of the samples is carried out by depositing 40 μl of HNTG buffer on each slide at the level of the tissue. The extracts are centrifuged at 14 000 rpm for 10 minutes and the supernatants are collected. The proteins are assayed and denatured with 4× Laemmli buffer by a heat treatment at 95° C. for 10 minutes.

Samples of 20 to 30 μg of protein were subjected to sodium dodecyl sulphate 7.5% polyacrylamide gel electrophoresis (SDS-PAGE) and then transferred onto a polyvinylidene difluoride membrane (PVDF Millipore Corpo.). Nonspecific binding is blocked with 2% skimmed milk in ECL buffer (20 mM Tris, pH 7.4, 150 mM NaCl, 0.05% Tween 20) for 2 hours, at room temperature.

The membranes are then incubated with the antibody Mab 1F1 diluted to 0.2 μg/ml in the blocking buffer overnight at 4° C. After washing with the ECL buffer —0.05% Tween 20, the bound proteins are detected by incubation with an anti-mouse antibody conjugated with a peroxidase and ECL chemiluminescent reagent (NEN Life Science Product).

The results presented in FIG. 2b show that the G3BP protein is overexpressed in moderately- and well-differentiated adenomas.

Example 4

Effect of the Microinjection of the Antibody Mab 1F1 on the Viability of Human Tumour Cells This example illustrates the property of the antibodies according to the invention to induce apoptosis in various types of tumour cells.

The monoclonal antibody Mab 1F1 was injected according to the protocol described below. The solution to be injected is dialysed against PBS, passed through a 0.45 µm UltraFree Millipore filter and centrifuged (5 min at 14 000 rpm) before being introduced into the microcapillary with the aid of a drawn out "microloader" tip (Roucaire). The injection time is set at 0.1 to 0.3 seconds and the injection pressure between 50 hPa and 150 hPa according to the size of the cells. About 200 cells were injected per condition.

The HCT116, H460, H1299, HeLa or HKe-3 cells were microinjected with 10 mg/ml of monoclonal antibody Mab 1F1 and then filmed and recorded by videomicroscopy (at 2 images per minute) for 3 days after injection. On reading the film, the development of the injected cells can be observed (divisions, cell deaths, morphological changes) and can be quantified (number of dividing or dead cells per hour). Only the cells which become detached from the support after condensation or fragmentation (events which can be observed for the apoptotic cells) are counted.

The results obtained with the injection of the antibody Mab 1F1 into the HCT 116 cells are presented in FIG. 3. A high percentage of induced cell death is observed from twelve hours after the injection of the antibody Mab 1F1, with a peak between 24 and 48 hours.

Different doses of antibody Mab 1F1 were tested in the HCT116 cells. From 10 mg/ml to 3 mg/ml, the effect of induction of cell death is equivalent, that is to say that the antibody Mab 1F1 induces cell death of at least 50% of the cells injected. At 1 mg/ml of antibody, the effect is considerably reduced.

If the HCT116 cells are injected with a mouse immunoglobulin at the concentration of 10 mg/ml as control, no death is observed and the injected cells continue to divide normally.

This toxic effect of the antibody Mab 1F1 in the HCT116 cells was confirmed by the use of the fluorescence "TUNEL" method, which makes it possible to specifically detect cuts in the DNA of cells entering into apoptosis:

The cells are inoculated on gridded glass coverslips (cellocates-Roucaire) and placed in 4-well plates. 2 days after inoculation, the cells are injected on these coverslips with the antibody Mab 1F1 or with a mouse immunoglobulin, as control, at 10 mg/ml. After injection, the cells are placed again in the oven for 40 h. They are then fixed with 4% formaldehyde for 15 min, permeabilized for 5 min with 0.2% triton x100 and rinsed several times with phosphate buffer. Double labelling is then carried out for 1 h at 37° C. with:

an anti-mouse antibody labelled with Texas Red diluted 1/400, which will stain the injected cells, Boerhinger "In situ cell death detection" kit which will specifically stain in green the cuts in the DNA of apoptotic cells.

The coverslips are then mounted on glass slides in mounting medium (Vectashield-Biosys).

Upon observation under fluorescent light, with the aid of filters which select the different colours, the injected cells on the one hand and the cells undergoing apoptosis on the other hand are counted.

Between 9 and 18% of HCT116 cells dead through apoptosis at time 40 h are thus obtained in 3 independent experiments. Under the same conditions, no death is observed of any HCT116 cell injected with the control immunoglobulin.

The recording experiments after microinjection of the antibody Mab 1F1 were reproduced with the H460, H1299, HeLa and HKe-3 cells with results similar to the graph presented in FIG. 3 showing that at least 50% of the injected cells die from 12 to 60 h after injection.

The "TUNEL" labelling experiments were carried out with the HCT116 and H460 cells and gave equivalent results (from 9 to 18% of the cells entering into apoptosis 40 hours after injection of the antibody).

Example 5

Effect of the Microinjection of the Antibody Mab 1F1 on the Viability and on the Proliferation of the Normal Human Fibroblasts NHDF 5.1—Effect of the Microinjection of the Antibody Mab 1F1 on the Viability of the Normal Human Fibroblasts NHDF The experiments for recording proliferating NHDF cells microinjected with the antibody Mab 1F1 show that no cell death is observed in the 60 h after injection and that the cells continue to divide normally.

5.2—Effect of the Microinjection of the Antibody Mab 1F1 on the Proliferation of Normal Human Fibroblasts NHDF Normal cells in culture require the supply of growth factors. If they are deprived of these factors, they enter into a "nonproliferation" phase called quiescence phase where they no longer replicate their DNA and can therefore no longer incorporate bromodeoxyuridine, a thymidine analogue added to the culture medium, which only proliferating cells can incorporate into their DNA.

When the antibody Mab 1F1 at the concentration of 10 mg/ml is microinjected into quiescent NHDF cells and these cells are again placed in a medium containing growth factors and bromodeoxyuridine (BrdU), a 33% inhibition of cell proliferation is observed after 24 h of contact followed by fixing and staining with the aid of an anti-BrdU antibody.

This inhibition is calculated by expressing the percentage of cells injected with the antibody Mab 1F1 and which incorporated BrdU relative to the percentage of cells injected with a mouse immunoblobulin and which incorporated BrdU (control).

Another anti-G3BP monoclonal antibody (11H7) was injected into the NHDF cells under the same conditions.

TABLE 1

Effect of the injection of antibodies specific for G3BP on the cell growth of NHDF cells

| Antibody injected | % BrdU incorporation |
|---|---|
| Mouse immunoglobulin (IgG) | 44.7 |
| Mab 1F1 | 29.7 |
| 11H7 | 30.3 |

It is observed that the immunoglobulin does not prevent cell proliferation whereas the antibody 11H7 has a similar effect to that of the antibody Mab 1F1, namely that they cause 32 to 33% inhibition of proliferation.

This inhibition is attributed to the blocking of the endogenous G3BP protein by the antibody Mab 1F1 or 11H7. In this regard, it is of interest to note that this stoppage of proliferation is only temporary in the normal cells NHDF and in no case causes cell death. Indeed, the cells continue their normal cycle when the antibody is naturally degraded in the cytoplasm (about 40 h after the injection).

The results presented in Examples 4 and 5 show that the antibody Mab 1F1 induces apoptosis in at least 50% of the human tumour cells tested in which G3BP is overexpressed but is found to be nontoxic when it is injected into the normal human cells where G3BP is weakly expressed. This effect in the tumour cells is apparently not linked to the state of activation of the ras genes. Moreover, the antibody Mab 1F1 causes a temporary termination—or a delay—in the proliferation of the normal cells NHDF when it is injected into quiescent cells.

Example 6

Cloning and Expression of a DNA Sequence Encoding an Intracellular Anti-G3BP Antibody from the Hybridoma G3B 1F1 1D1

This example describes the cloning and expression of a nucleic acid sequence encoding an intracellular antibody reproducing the properties of the monoclonal antibody Mab 1F1.

6.1—Preparation of the DNA Sequence

A DNA sequence encoding an intracellular antibody (ScFv fragment) is prepared according to the technique described in patent U.S. Pat. No. 4,946,778. This sequence is then placed under the control of a promoter which is functional in mammalian cells.

The poly A RNAs are isolated from a cellular culture of the hybridoma G3B 1F1 1D1, according to the technique described by Chirguin S. H. et al. (Biochemistry 18, 5294 (1979)). These RNAs are used for a Reverse-Transcription reaction with the aid of murine primers consisting of random hexanucleotides. The cDNAs obtained serve as template for two PCR reactions
  one intended to amplify the variable fragment of the heavy chain (VH) with VH specific primers,
  a second PCR making it possible to obtain the VL fragment, using a mixture of 10 primers derived from murine sequences.

Two fragments of 340 bp and 325 bp are thus obtained and assembled by means of a linker which allows correct positioning of the cDNA of VH in 5' of that of VL. PCR (Recombinant Phage Antibody System Mouse ScFv Module, Pharmacia, 27–9400-01).

The fused nucleic acid sequence VH-linker-VL is then inserted into a phagemid which allows the expression of the intracellular antibody. This expression easily allows the identification and the selection of the intracellular antibodies which correctly recognize the antigen. This step is carried out by selecting the antibodies capable of recognizing G3BP in an ELISA test (Recombinant Phage Antibody System Expression Module, Pharmacia, 27–9401-01).

6.2—Functional Evaluation of the Modified Intracellular Antibody

The sequence which encodes the modified anti-G3BP intracellular antibody is isolated from the phagemid by restriction, and then inserted into the vector SV2 (Schweighoffer et al., Science, 256, 825–827 (1992)) or pcDNA3 (InVitrogen, V790-20). The plasmid thus obtained is called pSV-ScFvG3BP or pcDNA3ScFvG3BP. The functional evaluation may be carried out by means of the tests described below.
  a) by microinjection into nonimmortalized mammalian cells NHDF and into transformed lines (HCT116, H460, Hke-3, H1299, Hela), examining apoptosis in the transformed lines according to the techniques described above and measuring the impact of the intracellular antibody on the cell viability by comparison with the activity of the antibody Mab 1F1.
  b) by a neoresistance test on the transformed lines and normal cells. The plasmid pcDNA3G3BP is transfected into the transformed lines (HCT116, Hke-3, H460, H1299, Hela) as well as into nontransformed human cells. Three days after transfection, the transformed cells are selected in the presence of geneticin. In this test, the single-chain antibody is compared with fragments of G3BP (whose corresponding nucleic acid sequences are contained in the same expression vectors) which inhibit the growth of the tumour cells.
  c) by the inhibition of the formation of clusters. The capacity of the single-chain antibody to inhibit the formation of clusters is determined according to the technique described in WO 94/29446. For the tests for reducing the tumour capacity, the effect may also be tested for in the case of transformation by oncogenes other than Ras.
  d) by testing for the impact of the expression of this ScFv on the activity for binding to the RNA and/or the endonucleolytic cleavage of the RNA by G3BP1. Indeed, apoptosis induced by microinjection of the monoclonal antibody Mab 1F1 can be explained either by dissociation of an interaction with a specific protein partner, or by modification of the activity for binding to RNA and/or for endoribonucleolytic cleavage. The ScFv antibody obtained may also be characterized by its capacity to modify these interactions.

Example 7

Identification of Another Domain for Recognition of the Antibody Mab 1F1 on the G3BP1 Protein. Comparison of Sequences Between the Human Proteins G3BP and G3BP2 (or G3BPh).

The G3BP protein is part of a family of proteins among which are the short G3BP2 proteins (AF 051311, Genbank) which exhibits 60.9% identity at the nucleotide level, and 58.9% at the protein level with G3BP, and the long G3BP2 protein (AB 014560, Genbank). The G2BP2 protein, long form, exhibits an insert of 99 nucleotides at 790 in the G3BP2 sequence (short form).

Comparison of the protein sequences between the G3BP and G3BP2 proteins reveals conservation of the principle domains of the protein, namely:
  1—an N-terminal region (exhibiting homologies with the NTF2 protein, Nuclear Transport Factor 2), a target for the monoclonal antibody Mab1F1,
  2—an acidic region,
  3—a region rich in PXXP motifs involved in the protein—protein interactions,
  4—a region comprising RNA recognition domains RRM, and auxiliary motifs, "RGG" (arginine, glycine, glycine) boxes.

Remarkably, the monoclonal antibody Mab1F1 is not capable of recognizing the recombinant protein G3BP2 (short form) in Western blot experiments. Comparison of the N-terminal sequences reveals several differences identified by diaereses in FIG. 4.

The use of peptides covering the different divergent regions has made it possible to specify the antibody recognition domain on the G3BP protein.

In a first instance, comparison of the protein sequences described above made it possible to synthesize various peptides (A–F):
  Peptide A: LLNQAPDMLHRFY (SEQ ID NO:5) amino acids 22–34 of the G3BP protein Peptide B: LLNKAPEYLHRFY (SEQ ID NO:6)
amino acids 22–34 of the G3BP2 protein
Peptide C: HGGLDSNGKPADAV (SEQ ID NO:7)
amino acids 42–55 of the G3BP protein
Peptide D: HGGVDASGKPQEAV (SEQ ID NO:8)
amino acids 42–55 of the G3BP2 protein
Peptide E: LLSNNNQALRRFMQ (SEQ ID NO:9)
amino acids 97–111 of the G3BP protein
Peptide F: HNDIFRYQDEVFG (SEQ ID NO:10)
amino acids 127–139 of the G3BP protein
Peptide E: LLSNNNQALRRFMQ
amino acids 97–111 of the G3BP protein
Peptide F: HNDIFRYQDEVFG
amino acids 127–139 of the G3BP protein
These peptides were then tested:
(i) for their capacity to recognize the antibody Mab1F1 in an ELISA test,
(ii) for their capacity to inhibit the recognition of the G3BP protein by the antibody Mab1F1 in Western blot experiments.

(i) Test of the Peptides A–F in an ELISA Test

The peptides in solution at 10 mg/ml in carbonate buffer (0.1 M, pH 9.6) were fixed by adsorption overnight at 4° C. on 96-well plates. After washing in PBS, the wells were saturated for 4 hours at room temperature in 1% PBS/BSA buffer. After three washes in PBS/0.05% Tween, the different wells were then brought into contact with dilutions of the purified antibody Mab1F1 in PBS/0.2% BSA (10 ng/ml to 1 pg/ml) for 1 hour at room temperature. After three washes in PBS buffer/0.05% Tween, the wells were incubated with a dilution of the peroxidase-coupled anti-mouse antibody (dilution 1/1000 in PBS/0.2% BSA) (Pharmacia) for 1 hour at room temperature. After three washes in PBS buffer/0.05% Tween, the colorimetric reaction was developed by mixing: 10 ml of $H_2O$, one OPD tablet, 100 ml of methanol, and 25 ml of $H_2O_2$. The reaction was stopped with 50 ml of 4 N H2SO4, and the spectrophotometric reading was carried out at 492 nm (reference filter 620 nm).

The results obtained show that peptide A is the most reactive in this test and is found to be capable of recognizing the antibody Mab1F1 in an ELISA test. These results indicate that the epitope recognized by the antibody Mab1F1 is situated in the domain defined by amino acids 22 to 34 of G3BP. The same experiments carried out with the antibody 1E1 gave identical results.

(ii) Test of the Peptides A–F for Their Capacity to Inhibit the Recognition of the G3BP Protein by the Antibody Mab1F1 in Western Blot Experiments The detection of the proteins by Western blotting was carried out according to the technique described in Example 2 (2.1: Detection of the proteins by Western blotting). For the competitions, the antibody was preincubated for two hours at 37° C. with a dilution of the peptide before being brought into contact with the membrane. For each peptide, two concentrations were tested: molar excess of 10 and of 100 relative to the antibody. The visualization was then carried out as described in Example 2.1.

The results obtained show that the peptides A and C are capable of displacing the interaction between the G3BP protein and the antibody Mab1F1 (mainly with a 100× molar excess).

All these results show the peptide A (amino acids 22–34 of G3BP) and the peptide C (amino acids 42–55 of G3BP) as corresponding to G3BP domains involved in the recognition with the antibody Mab1F1.

Sequence comparison between G3BP and G3BP2 short form therefore allowed the identification of various peptides and the demonstration of their role in the control of apoptosis by G3BP; these results make it possible to envisage various applications and in particular the use these peptides for molecular modelling, in order to obtain small molecules which mimic the effects of these peptides or of polypeptides containing them. Moreover, these peptides can be used to displace an interaction of the G3BP protein with a cellular partner; this cellular partner may be G3BP itself since it has been shown that the protein is capable of forming a dimer; this partner may also be a known partner (RasGAP) or a newly identified partner. To this effect, these peptides coupled to a resin may be used for the search for the cellular partner of G3BP. Finally, screening of molecules of therapeutic interest may be established on the basis of the inhibition of a protein—protein interaction.

Example 8

Construction of Fragments of G3BP1 and Apoptotic Activity of These Fragments

In the light of the results obtained in Example 7, plasmids allowing the expression of N-terminal fragments of G3BP were constructed in order to test the apoptotic activity of these fragments. For that, the fragments were amplified by PCR from the following primers:
A—Oligonucleotide 5' in G3BP (Nucleotide 1)
SEQ ID NO:11
cccgtcgacatggtgatggagaagcctagtcccctg
B—Oligonucleotide 5' in G3BP (Nucleotide 42)
SEQ ID NO:12
cccgggtcgactttgtgagacagtattacaca
C—Oligonucleotide 3' in G3BP (Nucleotide 150)
SEQ ID NO:13
cccgggtgcggccgcctttccatttgaatccaatcc Fragments (1–150) and (42–150) were amplified by PCR (30 cycles at 50° C.), hydrolysed with the restriction enzymes Sal1 and Not1, and then inserted into the commercial vector pCMV/cyto (Invitrogen, pShooter Vector manual II, version C).

The sequences of the fragments obtained are described below: the sequences obtained from the vector and which will be translated are written in uppercase letters, the sequences of G3BP cDNA are indicated in lowercase letters. The underlined regions correspond to the sequences of the vector encoding Tag myc).

(Fragment 1–150)

SEQ ID NO:14
5' ATGGCCCAGGTGCAGCTGCAGGTCatg-gtgatggagaagcctagtcccctgctggtc gggcgggaatttgtgagacagtat-tacacactgctgaaccaggcccagacatgctgcatagattttatggaaag aactcttcttatgtccatggggattg-gattcaaatggaaagGCGGCCGCAGAACAAAAACT CATCT-CAGAAGAGGATCTGAATGGGGCCGCATAG 3'

The corresponding polypeptide is presented below. This polypeptide comprises the fragment corresponding to amino acids 1 to 50 of the G3BP protein whose sequence is presented in the sequence SEQ ID No. 1; this fragment appears below in bold characters.

SEQ ID NO:15
MAQVQLQVM-VMEKPSPLLVGREFVRQYYTLLNQAPDM-LHRFYGKNSSY VHGGLDSNGKAAA EQKLISEEDLN-GAA (Fragment 42–150)

SEQ ID NO:16
5'ATGGCCCAGGTGCAGCTGCAG-GTCtttgtgagacagtattacacactgctgaaccagg ccccagacatgctg-catagattttatggaaagaactcttcttatgtccatgggggattggattcaaatggaaagGC
GGCCGCAGAACAAAAACTCATCTCAGAA-
GAGGATCTGAATGGGGC CGCATAG 3'

The corresponding polypeptide is presented below. This polypeptide comprises the fragment corresponding to amino acids 15 to 50 of the G3BP protein whose sequence is presented in the sequence SEQ ID No. 1; this fragment appears below in bold characters.

SEQ ID NO:17
MAQVQLQVFVRQYYTLLNQAPDMLHR-
FYGKNSSYVHGGLDSNGKAAAE QKLISEEDLNGAA

The constructs comprising fragments 1–150 and 42–150 of the nucleotide sequence of G3BP were transfected into the transformed lines NIH3T3Ras and NIH3T3Raf. These lines were obtained after transformation of NIH3T3 cells by the oncogene Ki-RasVal12, or with the oncogenic viral form of v-Raf.

For the detection of apoptosis, 2 mg of plasmid were transfected with lipofectamine (Gibco-BRL), and the apoptosis was measured 48 hours after transfection by FACS analysis. The cells undergoing apoptosis correspond to the cells in the subG1 phase.

Under these conditions, the construct expressing fragment 1–150 of the G3BP sequence (encoding the fragment of G3BP comprising amino acids 1 to 50) is capable of inducing apoptosis (factor of 4), whereas the construct expressing fragment 42–150 of the G3BP sequence (encoding the fragment of G3BP comprising amino acids 15 to 50) does not exhibit this property.

These results designate the domain corresponding to amino acids 1 to 14 of G3BP as a domain involved in the induction of apoptosis. The identification of this G3BP domain and the demonstration of the role of the polypeptides comprising the domain corresponding to amino acids 1 to 14 of G3BP in the control of apoptosis makes it possible to envisage the use of these polypeptides for the prevention, improvement and/or treatment of pathologies involving cell hyperproliferation.

Example 9

Construction of Fusion Proteins with Fragments of huG3BP1

Constructs allowing the expression of the peptides identified in Example 7 are produced. The sequences corresponding to the peptides are fused with the GST (Glutathione S-transferase) protein in order to stabilize them.

Sequences of the Oligonucleotides:

Each sense oligonucleotide is bordered in 5' by 4 nucleotides in order to reconstitute an NcoI site, and in 3' by a stop codon (TAA) and a nucleotide so as to form a BamHI site.

SEQ ID NO:18
sq22s: tatgctgctgaaccaggccccagacatgctgcatagattttattaag

SEQ ID NO:19
sq22 as: gatccttaataaaatctatgcagcat-
gtctggggcctggttcagcagca
(Sequence 66–105)

SEQ ID NO:20
sq 44g1s: tatgggattggattcaaatggaaagccagcagatgcagtctaag

SEQ ID NO:21
sq44g1as: gatccttagactgcatctgctggctttccatttgaatccaatccca
(Sequence 130–166)

SEQ ID NO:22
sq44g2s: tatgggagtagatgctagtggaaagccccaggaagctgtttaag

SEQ ID NO:23
sq44g2as: gatccttaaacagcttcctggggctttccactagcatctactccca
(Sequence 130–166)

SEQ ID NO:24
sq64s: tatgcagaaagaaatccacaggaaagtgatgtcacaaaacttctaag

SEQ ID NO:25
sq64as: gatccttagaagttttgtgacatcactttcctgtggatttctttctgca
(Sequence 172–211)

SEQ ID NO:26
sq65s: tatgaaagtgatgtcacaaaacttcaccaactgctaag

SEQ ID NO:27
sq65as: gatccttagcagttggtgaagttttgtgacatcactttca
(Sequence 190–220)

The oligonucleotides are hybridized in pairs by cooling from 80° C. to room temperature, phosphorylated with T4 Polynucleotide Kinase (Boehringer), and inserted into the vector "pBCcol1GSTfusion" at the NcoI and BamHI sites. This vector allows the expression, in eukaryotic cells, of a GST fusion protein using an SV40 promoter (Genbank, X78316). The plasmids are then transfected into human tumour lines, Hela and H1299 (described in materials and methods); the apoptosis induced is measured by FACS as described in Example 8.

What is claimed is:

1. The antibody Mab 1F1, secreted by the hybridoma line G3BP 1F1 1D1 deposited on 9 Jun. 1998 at the C.N.C.M. under the number I-2038.

2. Hybridoma line G3BP 1 F1 1 D1 deposited on 9 Jun. 1998 at the C.N.C.M. under the deposit number I-2038.

3. Monoclonal antibody directed against the protein of SEQ ID NO:1 and capable of inducing apoptosis in various types of tumor cells, wherein the antibody recognizes an epitope between amino acids 22–34 of SEQ ID NO:1.

4. Pharmaceutical composition comprising a therapeutically effective quantity of the monoclonal antibodies according to claim 3, the said quantity being therapeutically effective for inducing apoptosis in tumor cells.

5. Hybridoma line capable of secreting monoclonal antibodies according to claim 3.

* * * * *

SEQUENCE LISTING

<160> NUMBER OF SEQ ID NOS: 27

<210> SEQ ID NO 1
<211> LENGTH: 466
<212> TYPE: PRT
<213> ORGANISM: homo sapiens

<400> SEQUENCE: 1

Met Val Met Glu Lys Pro Ser Pro Leu Leu Val Gly Arg Glu Phe Val
1               5                   10                  15

Arg Gln Tyr Tyr Thr Leu Leu Asn Gln Ala Pro Asp Met Leu His Arg
            20                  25                  30

Phe Tyr Gly Lys Asn Ser Ser Tyr Val His Gly Gly Leu Asp Ser Asn
        35                  40                  45

Gly Lys Pro Ala Asp Ala Val Tyr Gly Gln Lys Glu Ile His Arg Lys

-continued

```
                50                  55                  60
Val Met Ser Gln Asn Phe Thr Asn Cys His Thr Lys Ile Arg His Val
 65                  70                  75                  80

Asp Ala His Ala Thr Leu Asn Asp Gly Val Val Gln Val Met Gly
                 85                  90                  95

Leu Leu Ser Asn Asn Asn Gln Ala Leu Arg Arg Phe Met Gln Thr Phe
                100                 105                 110

Val Leu Ala Pro Glu Gly Ser Ala Asn Lys Phe Tyr Val His Asn
                115                 120                 125

Asp Ile Arg Tyr Gln Asp Glu Val Phe Gly Gly Phe Val Thr Glu Pro
130                 135                 140

Gln Glu Glu Ser Glu Glu Val Glu Glu Pro Glu Glu Arg Gln Gln
145                 150                 155                 160

Thr Pro Glu Val Val Pro Asp Asp Ser Gly Thr Phe Tyr Asp Gln Ala
                165                 170                 175

Val Val Ser Asn Asp Met Glu Glu His Leu Glu Glu Pro Val Ala Glu
                180                 185                 190

Pro Glu Pro Asp Pro Glu Pro Glu Gln Glu Pro Val Ser Glu
                195                 200                 205

Ile Gln Glu Glu Lys Pro Glu Pro Val Leu Glu Glu Thr Ala Pro Glu
210                 215                 220

Asp Ala Gln Lys Ser Ser Ser Pro Ala Pro Ala Asp Ile Ala Gln Thr
225                 230                 235                 240

Val Gln Glu Asp Leu Arg Thr Phe Ser Trp Ala Ser Val Thr Ser Lys
                245                 250                 255

Asn Leu Pro Pro Ser Gly Ala Val Pro Val Thr Gly Ile Pro Pro His
                260                 265                 270

Val Lys Val Pro Ala Ser Gln Pro Arg Pro Glu Ser Lys Pro Glu
                275                 280                 285

Ser Gln Ile Pro Pro Gln Arg Pro Gln Arg Asp Gln Arg Val Arg Glu
                290                 295                 300

Gln Arg Ile Asn Ile Pro Pro Gln Arg Gly Pro Arg Pro Ile Arg Glu
305                 310                 315                 320

Ala Gly Glu Gln Gly Asp Ile Glu Pro Arg Arg Met Val Arg His Pro
                325                 330                 335

Asp Ser His Gln Leu Phe Ile Gly Asn Leu Pro His Glu Val Asp Lys
                340                 345                 350

Ser Glu Leu Lys Asp Phe Gln Ser Tyr Gly Asn Val Val Glu Leu
                355                 360                 365

Arg Ile Asn Ser Gly Gly Lys Leu Pro Asn Phe Gly Phe Val Val Phe
370                 375                 380

Asp Asp Ser Glu Pro Val Gln Lys Val Leu Ser Asn Arg Pro Ile Met
385                 390                 395                 400

Phe Arg Gly Glu Val Arg Leu Asn Val Glu Glu Lys Lys Thr Arg Ala
                405                 410                 415

Ala Arg Glu Gly Asp Arg Arg Asp Asn Arg Leu Arg Gly Pro Gly Gly
                420                 425                 430

Pro Arg Gly Gly Leu Gly Gly Gly Met Arg Gly Pro Pro Arg Gly Gly
                435                 440                 445

Met Val Gln Lys Pro Gly Phe Gly Val Gly Arg Gly Leu Ala Pro Arg
                450                 455                 460

Gln Glx
465
```

<210> SEQ ID NO 2
<211> LENGTH: 2129
<212> TYPE: DNA
<213> ORGANISM: homo sapiens

<400> SEQUENCE: 2

| | | | | | |
|---|---|---|---|---|---|
| gcttgcctgt | caggtcgact | ctagagcccg | ggtaccgagc | tcgaattcgg | cggggtttgt | 60 |
| actatcctcg | gtgctgtggt | gcagagctag | ttcctctcca | gctcagccgc | gtaggtttgg | 120 |
| acatatttac | tcttttcccc | ccaggttgaa | ttgaccaaag | caatggtgat | ggagaagcct | 180 |
| agtcccctgc | tggtcgggcg | ggaatttgtg | agacagtatt | acacactgct | gaaccaggcc | 240 |
| ccagacatgc | tgcatagatt | ttatggaaag | aactcttctt | atgtccatgg | gggattggat | 300 |
| tcaaatggaa | agccagcaga | tgcagtctac | ggacagaaag | aaatccacag | gaaagtgatg | 360 |
| tcacaaaact | tcaccaactg | ccacaccaag | attcgccatg | ttgatgctca | tgccacgcta | 420 |
| aatgatggtg | tggtagtcca | ggtgatgggg | cttctctcta | caacaaccca | ggctttgagg | 480 |
| agattcatgc | aaacgtttgt | ccttgctcct | gagggtctg | ttgcaaataa | attctatgtt | 540 |
| cacaatgata | tcttcagata | ccaagatgag | gtctttggtg | ggtttgtcac | tgagcctcag | 600 |
| gaggagtctg | aagaagaagt | agaggaacct | gaagaaagca | gcaaacacct | gaggtggtac | 660 |
| ctgatgattc | tggaactttc | tatgatcagg | cagttgtcag | taatgacatg | gaagaacatt | 720 |
| tagaggagcc | tgttgctgaa | ccagagcctg | atcctgaacc | agaaccagaa | caagaacctg | 780 |
| tatctgaaat | ccaagaggaa | aagcctgagc | cagtattaga | gaaactgccc | ctgaggatg | 840 |
| ctcagaagag | ttcttctcca | gcacctgcag | acatagctca | gacagtacag | gaagacttga | 900 |
| ggacattttc | ttgggcatct | gtgaccagta | agaatcttcc | acccagtgga | gctgttccag | 960 |
| ttactgggat | accacctcat | gttgttaaag | taccagcttc | acagcccgt | ccagagtcta | 1020 |
| agcctgaatc | tcagattcca | ccacaaagac | ctcagcggga | tcaaagagtg | cgagaacaac | 1080 |
| gaataaatat | tcctccccaa | agggaccca | gaccaatccg | tgaggctggt | gagcaaggtg | 1140 |
| acattgaacc | ccgaagaatg | gtgagacacc | ctgacagtca | ccaactcttc | attggcaacc | 1200 |
| tgcctcatga | agtggacaaa | tcagagctta | agatttcttt | tcaaagttat | ggaaacgtgg | 1260 |
| tggagttgcg | cattaacagt | ggtgggaaat | acccaatttt | tggttttgtt | gtgtttgatg | 1320 |
| attctgagcc | tgttcagaaa | gtccttagca | acaggcccat | catgttcaga | ggtgaggtcc | 1380 |
| gtctgaatgt | cgaagagaag | aagactcgag | ctgccaggga | aggcgaccga | cgagataatc | 1440 |
| gccttcgggg | acctggaggc | cctcgaggtg | ggctgggtgg | tggaatgaga | ggccctcccc | 1500 |
| gtggaggcat | ggtgcagaaa | ccaggatttg | gagtgggaag | ggggcttgcg | ccacggcagt | 1560 |
| aatcttcatg | gatcttcatg | cagccataca | aaccctggtt | ccaacagaat | ggtgaatttt | 1620 |
| cgacagcctt | tggtatcttg | gagtatgacc | ccagtctgtt | ataaactgct | taagtttgta | 1680 |
| taatttact | tttttgtgt | gttaatggtg | tgtgctccct | ctccctctct | tcccttctcct | 1740 |
| gacctttagt | ctttcacttc | caatttgtg | gaatgatatt | ttaggaataa | cggactttta | 1800 |
| cccgaattcg | taatcatggt | catagctgtt | tccgtgtgaa | attgttatcc | gctcacaatt | 1860 |
| ccacacaaca | tacgagccgg | aagcataaag | tgtaaagcct | ggggtgccta | atgagtgagc | 1920 |
| taactcacat | taattgcgtt | gcgctcactg | cccgctttcc | agtcgggaaa | cctgtcgtgc | 1980 |
| cagcgcatta | atgaatcggc | caacgcgcgg | ggagaggcgg | tttgcgtatt | gggcgccagg | 2040 |
| gtggtttttct | tttcaccagt | gagacgggca | acagctgatt | gcccttcacc | gctggccctg | 2100 |

-continued agagagttgc agcaagcggt ccacgctgg                                    2129

<210> SEQ ID NO 3
<211> LENGTH: 143
<212> TYPE: PRT
<213> ORGANISM: homo sapiens

<400> SEQUENCE: 3

Met Val Met Glu Lys Pro Ser Pro Leu Leu Val Gly Arg Glu Phe Val
1               5                   10                  15

Arg Gln Tyr Tyr Thr Leu Leu Asn Gln Ala Pro Asp Met Leu His Arg
            20                  25                  30

Phe Tyr Gly Lys Asn Ser Ser Tyr Val His Gly Gly Leu Asp Ser Asn
        35                  40                  45

Gly Lys Pro Ala Asp Ala Val Tyr Gly Gln Lys Glu Ile His Arg Lys
    50                  55                  60

Val Met Ser Gln Asn Phe Thr Asn Cys His Thr Lys Ile Arg His Val
65                  70                  75                  80

Asp Ala His Ala Thr Leu Asn Asp Gly Val Val Gln Val Met Gly
                85                  90                  95

Leu Leu Ser Asn Asn Asn Gln Ala Leu Arg Arg Phe Met Gln Thr Phe
                100                 105                 110

Val Leu Ala Pro Glu Gly Ser Val Ala Asn Lys Phe Tyr Val His Asn
            115                 120                 125

Asp Ile Phe Arg Tyr Gln Asp Glu Val Phe Gly Gly Phe Val Thr
        130                 135                 140

<210> SEQ ID NO 4
<211> LENGTH: 143
<212> TYPE: PRT
<213> ORGANISM: homo sapiens

<400> SEQUENCE: 4

Met Val Met Glu Lys Pro Ser Pro Leu Leu Val Gly Arg Glu Phe Val
1               5                   10                  15

Arg Gln Tyr Tyr Thr Leu Leu Asn Lys Ala Pro Glu Tyr Leu His Arg
            20                  25                  30

Phe Tyr Gly Arg Asn Ser Ser Tyr Val His Gly Gly Val Asp Ala Ser
        35                  40                  45

Gly Lys Pro Gln Glu Ala Val Tyr Gly Gln Asn Asp Ile His His Lys
    50                  55                  60

Val Leu Ser Leu Asn Phe Ser Glu Cys His Thr Lys Ile Arg His Val
65                  70                  75                  80

Asp Ala His Ala Thr Leu Ser Asp Gly Val Val Gln Val Met Gly
                85                  90                  95

Leu Leu Ser Asn Ser Gly Gln Pro Glu Arg Lys Phe Met Gln Thr Phe
                100                 105                 110

Val Leu Ala Pro Glu Gly Ser Val Pro Asn Lys Phe Tyr Val His Asn
            115                 120                 125

Asp Met Phe Arg Tyr Glu Asp Glu Val Phe Gly Asp Ser Glu Pro
        130                 135                 140

<210> SEQ ID NO 5
<211> LENGTH: 13
<212> TYPE: PRT
<213> ORGANISM: Artificial
<220> FEATURE:
<223> OTHER INFORMATION: amino acids 22-34 of the G3BP protein

```
<400> SEQUENCE: 5

Leu Leu Asn Gln Ala Pro Asp Met Leu His Arg Phe Tyr
1               5                   10

<210> SEQ ID NO 6
<211> LENGTH: 13
<212> TYPE: PRT
<213> ORGANISM: Artificial
<220> FEATURE:
<223> OTHER INFORMATION: amino acids 22-34 of the G3BP2 protein

<400> SEQUENCE: 6

Leu Leu Asn Lys Ala Pro Glu Tyr Leu His Arg Phe Tyr
1               5                   10

<210> SEQ ID NO 7
<211> LENGTH: 14
<212> TYPE: PRT
<213> ORGANISM: artificial
<220> FEATURE:
<223> OTHER INFORMATION: amino acids 42-55 of the G3BP protein

<400> SEQUENCE: 7

His Gly Gly Leu Asp Ser Asn Gly Lys Pro Ala Asp Ala Val
1               5                   10

<210> SEQ ID NO 8
<211> LENGTH: 14
<212> TYPE: PRT
<213> ORGANISM: Artificial
<220> FEATURE:
<223> OTHER INFORMATION: amino acids 42-55 of the G3BP2 protein

<400> SEQUENCE: 8

His Gly Gly Val Asp Ala Ser Gly Lys Pro Gln Glu Ala Val
1               5                   10

<210> SEQ ID NO 9
<211> LENGTH: 14
<212> TYPE: PRT
<213> ORGANISM: artificial
<220> FEATURE:
<223> OTHER INFORMATION: amino acids 97-111 of the G3BP protein

<400> SEQUENCE: 9

Leu Leu Ser Asn Asn Asn Gln Ala Leu Arg Arg Phe Met Gln
1               5                   10

<210> SEQ ID NO 10
<211> LENGTH: 13
<212> TYPE: PRT
<213> ORGANISM: artificial
<220> FEATURE:
<223> OTHER INFORMATION: amino acids 127-139 of the G3BP protein

<400> SEQUENCE: 10

His Asn Asp Ile Phe Arg Tyr Gln Asp Glu Val Phe Gly
1               5                   10

<210> SEQ ID NO 11
<211> LENGTH: 36
<212> TYPE: DNA
<213> ORGANISM: artificial
<220> FEATURE:
<223> OTHER INFORMATION: primer A
```

```
<400> SEQUENCE: 11
cccgtcgaca tggtgatgga gaagcctagt cccctg                                36

<210> SEQ ID NO 12
<211> LENGTH: 32
<212> TYPE: DNA
<213> ORGANISM: artificial
<220> FEATURE:
<223> OTHER INFORMATION: primer B

<400> SEQUENCE: 12
cccgggtcga ctttgtgaga cagtattaca ca                                    32

<210> SEQ ID NO 13
<211> LENGTH: 36
<212> TYPE: DNA
<213> ORGANISM: artificial
<220> FEATURE:
<223> OTHER INFORMATION: primer C

<400> SEQUENCE: 13
cccgggtgcg gccgcctttc catttgaatc caatcc                                36

<210> SEQ ID NO 14
<211> LENGTH: 228
<212> TYPE: DNA
<213> ORGANISM: artificial
<220> FEATURE:
<223> OTHER INFORMATION: cDNA fragment containing vector and G3BP
      sequences

<400> SEQUENCE: 14
atggcccagg tgcagctgca ggtcatggtg atggagaagc ctagtcccct gctggtcggg      60
cgggaatttg tgagacagta ttacacactg ctgaaccagg ccccagacat gctgcataga     120
ttttatggaa agaactcttc ttatgtccat ggggggattgg attcaaatgg aaaggcggcc    180
gcagaacaaa aactcatctc agaagaggat ctgaatgggg ccgcatag                  228

<210> SEQ ID NO 15
<211> LENGTH: 75
<212> TYPE: PRT
<213> ORGANISM: artificial
<220> FEATURE:
<223> OTHER INFORMATION: amino acids of 1-50 of the G3BP protein

<400> SEQUENCE: 15

Met Ala Gln Val Gln Leu Gln Val Met Val Met Glu Lys Pro Ser Pro
1               5                   10                  15

Leu Leu Val Gly Arg Glu Phe Val Arg Gln Tyr Tyr Thr Leu Leu Asn
            20                  25                  30

Gln Ala Pro Asp Met Leu His Arg Phe Tyr Gly Lys Asn Ser Ser Tyr
        35                  40                  45

Val His Gly Gly Leu Asp Ser Asn Gly Lys Ala Ala Glu Gln Lys
    50                  55                  60

Leu Ile Ser Glu Glu Asp Leu Asn Gly Ala Ala
65                  70                  75

<210> SEQ ID NO 16
<211> LENGTH: 186
<212> TYPE: DNA
<213> ORGANISM: artificial
<220> FEATURE:
<223> OTHER INFORMATION: cDNA fragment containing vector and G3BP
```

-continued sequences

<400> SEQUENCE: 16
atggcccagg tgcagctgca ggtctttgtg agacagtatt acacactgct gaaccaggcc      60
ccagacatgc tgcatagatt ttatggaaag aactcttctt atgtccatgg gggattggat     120
tcaaatggaa aggcggccgc agaacaaaaa ctcatctcag aagaggatct gaatggggcc     180
gcatag                                                                186

<210> SEQ ID NO 17
<211> LENGTH: 61
<212> TYPE: PRT
<213> ORGANISM: artificial
<220> FEATURE:
<223> OTHER INFORMATION: amino acids 15-50 of the G3BP protein

<400> SEQUENCE: 17

Met Ala Gln Val Gln Leu Gln Val Phe Val Arg Gln Tyr Tyr Thr Leu
1               5                   10                  15

Leu Asn Gln Ala Pro Asp Met Leu His Arg Phe Tyr Gly Lys Asn Ser
            20                  25                  30

Ser Tyr Val His Gly Gly Leu Asp Ser Asn Gly Lys Ala Ala Ala Glu
        35                  40                  45

Gln Lys Leu Ile Ser Glu Glu Asp Leu Asn Gly Ala Ala
    50                  55                  60

<210> SEQ ID NO 18
<211> LENGTH: 47
<212> TYPE: DNA
<213> ORGANISM: artificial
<220> FEATURE:
<223> OTHER INFORMATION: sq22s oligonucleotide

<400> SEQUENCE: 18
tatgctgctg aaccaggccc cagacatgct gcatagattt tattaag                    47

<210> SEQ ID NO 19
<211> LENGTH: 49
<212> TYPE: DNA
<213> ORGANISM: artificial
<220> FEATURE:
<223> OTHER INFORMATION: sq22as oligonucleotide

<400> SEQUENCE: 19
gatccttaat aaaatctatg cagcatgtct ggggcctggt tcagcagca                  49

<210> SEQ ID NO 20
<211> LENGTH: 44
<212> TYPE: DNA
<213> ORGANISM: artificial
<220> FEATURE:
<223> OTHER INFORMATION: sq44g1s oligonucleotide

<400> SEQUENCE: 20
tatgggattg gattcaaatg gaaagccagc agatgcagtc taag                       44

<210> SEQ ID NO 21
<211> LENGTH: 46
<212> TYPE: DNA
<213> ORGANISM: artificial
<220> FEATURE:
<223> OTHER INFORMATION: sq44g1as oligonucleotide

<400> SEQUENCE: 21

```
gatccttaga ctgcatctgc tggctttcca tttgaatcca atccca                    46

<210> SEQ ID NO 22
<211> LENGTH: 44
<212> TYPE: DNA
<213> ORGANISM: artificial
<220> FEATURE:
<223> OTHER INFORMATION: sq44g2s oligonucleotide

<400> SEQUENCE: 22
tatgggagta gatgctagtg aaagcccca ggaagctgtt taag                       44

<210> SEQ ID NO 23
<211> LENGTH: 46
<212> TYPE: DNA
<213> ORGANISM: artificial
<220> FEATURE:
<223> OTHER INFORMATION: sq44g2as oligonucleotide

<400> SEQUENCE: 23
gatccttaaa cagcttcctg gggctttcca ctagcatcta ctccca                    46

<210> SEQ ID NO 24
<211> LENGTH: 47
<212> TYPE: DNA
<213> ORGANISM: artificial
<220> FEATURE:
<223> OTHER INFORMATION: sq64s oligonucleotide

<400> SEQUENCE: 24
tatgcagaaa gaaatccaca ggaaagtgat gtcacaaaac ttctaag                   47

<210> SEQ ID NO 25
<211> LENGTH: 49
<212> TYPE: DNA
<213> ORGANISM: artificial
<220> FEATURE:
<223> OTHER INFORMATION: sq64as oligonucleotide

<400> SEQUENCE: 25
gatccttaga agttttgtga catcactttc ctgtggattt ctttctgca                 49

<210> SEQ ID NO 26
<211> LENGTH: 38
<212> TYPE: DNA
<213> ORGANISM: artificial
<220> FEATURE:
<223> OTHER INFORMATION: sq65s oligonucleotide

<400> SEQUENCE: 26
tatgaaagtg atgtcacaaa acttcaccaa ctgctaag                             38

<210> SEQ ID NO 27
<211> LENGTH: 40
<212> TYPE: DNA
<213> ORGANISM: artificial
<220> FEATURE:
<223> OTHER INFORMATION: sq65as oligonucleotide

<400> SEQUENCE: 27
gatccttagc agttggtgaa gttttgtgac atcactttca                           40
```